US010398823B2

United States Patent
Heinemann

(10) Patent No.: US 10,398,823 B2
(45) Date of Patent: Sep. 3, 2019

(54) EXTRACORPOREAL BLOOD TREATMENT SYSTEM WITH INTEGRATED DISINFECTION CASE

(71) Applicant: B. BRAUN AVITUM AG, Melsungen (DE)

(72) Inventor: Thore Heinemann, Söhrewald-Wellerode (DE)

(73) Assignee: B. Braun Avitum AG (DE)

( * ) Notice: Subject to any disclaimer, the term of this patent is extended or adjusted under 35 U.S.C. 154(b) by 93 days.

(21) Appl. No.: 15/196,846

(22) Filed: Jun. 29, 2016

(65) Prior Publication Data
US 2017/0014564 A1   Jan. 19, 2017

(30) Foreign Application Priority Data
Jul. 14, 2015   (DE) .................... 20 2015 103 684 U

(51) Int. Cl.
*A61M 1/16*   (2006.01)

(52) U.S. Cl.
CPC .......... *A61M 1/168* (2013.01); *A61M 1/1601* (2014.02); *A61M 1/169* (2013.01); *A61M 1/1682* (2014.02); *A61M 1/1686* (2013.01); *A61M 2205/14* (2013.01); *A61M 2205/3331* (2013.01); *A61M 2205/3379* (2013.01); *A61M 2209/10* (2013.01)

(58) Field of Classification Search
CPC combination set(s) only.
See application file for complete search history.

(56) References Cited

U.S. PATENT DOCUMENTS

| | | | |
|---|---|---|---|
| 4,366,051 A | 12/1982 | Fischel | |
| 5,304,349 A | 4/1994 | Polaschegg | |
| 5,591,344 A * | 1/1997 | Kenley | A61L 2/04 210/134 |
| 5,647,984 A * | 7/1997 | Hovland | A61M 1/1686 210/175 |
| 5,895,578 A | 4/1999 | Simard et al. | |
| 6,379,617 B1 | 4/2002 | Spickermann | |

(Continued)

FOREIGN PATENT DOCUMENTS

| | | |
|---|---|---|
| CN | 102293494 | 12/2011 |
| DE | 25 59 241 | 7/1976 |

(Continued)

OTHER PUBLICATIONS

German Search Report with translation for DE 20 2015 103 684.1 dated Feb. 16, 2016.

(Continued)

*Primary Examiner* — Dirk R Bass
(74) *Attorney, Agent, or Firm* — RatnerPrestia

(57) ABSTRACT

An extracorporeal blood purification system with at least one extracorporeal blood purification apparatus, preferably dialysis machine, which is prepared to go through a centrally controlled disinfection process for a blood purification process, as well as with an internal fluid line system which is disinfected at least during the disinfection process by a disinfectant, including an internal or external disinfecting or cleaning case which is at least during the disinfection process via at least one case connection connected to the internal fluid conduit system to receive disinfectant.

10 Claims, 2 Drawing Sheets

(56) References Cited

U.S. PATENT DOCUMENTS

| | | | |
|---|---|---|---|
| 8,182,691 B2 | 5/2012 | Stahl | |
| 2002/0045851 A1* | 4/2002 | Suzuki | A61M 1/28 604/28 |
| 2005/0000828 A1* | 1/2005 | Carson | C02F 1/4672 205/701 |
| 2012/0167997 A1 | 7/2012 | Brensing et al. | |

FOREIGN PATENT DOCUMENTS

| | | |
|---|---|---|
| DE | 7812762 | 4/1978 |
| DE | 7814376 | 8/1978 |
| DE | 41 38 140 | 5/1993 |
| DE | 295 03 691 | 6/1995 |
| DE | 196 40 840 | 4/1998 |
| DE | 697 15 969 | 6/2003 |
| DE | 103 19 220 | 7/2004 |
| DE | 10 2007 022 547 | 11/2008 |
| DE | 10 2007 044 647 | 3/2009 |
| DE | 10 2009 026 375 | 2/2011 |
| DE | 10 2013 107 323 | 1/2015 |
| EP | 1 491 222 | 12/2004 |

OTHER PUBLICATIONS

European Search Report with translation for EP 16 17 6789 dated Dec. 8, 2016.

* cited by examiner

EXTRACORPOREAL BLOOD TREATMENT SYSTEM WITH INTEGRATED DISINFECTION CASE

CROSS REFERENCE TO RELATED APPLICATIONS

This application claims priority to German Application DE 20 2015 103 684.1 filed Jul. 14, 2015, the contents of such application being incorporated by reference herein.

FIELD OF THE INVENTION

The present invention relates to an extracorporeal blood treatment system, especially a dialysis system in accordance with the preamble of the independent claim, comprising at least one extracorporeal blood treatment machine such as a dialysis machine which is prepared, inter alia, with connectors, conduits and an appropriate controller to undergo a centrally controlled disinfection process following a blood purification process.

BACKGROUND OF THE INVENTION

In extracorporeal blood treatment systems, preferably blood purification systems such as dialysis systems, at least one, usually plural blood treatment/blood purification/dialysis machines are arranged. The individual dialysis machines and the dedicated components undergo a disinfection process after each dialysis operating cycle which is composed of different operating phases. In said disinfection process all parts of the dialysis system that have been in direct or else indirect contact with fluids such as blood or dialysis fluid during the operating cycle and that are consequently contaminated are disinfected. Those parts include, for example, all fluid lines, heat exchangers and valves which have transported or conveyed fluids and, respectively, have been in contact with the latter during the operating cycle.

Further, also objects that have served as accessories during the dialysis process are disinfected in the wake of the dialysis operating cycle. These accessories include instruments/parts/means/materials being required, apart from the dialysis machine, for implementing the dialysis process. In this context, scissors, clamps such as hose clamps, individual components of the dialysis filter, folding mechanisms, hose/line connectors and cover films are mentioned by way of example. The spectrum of the accessories cannot be reduced to the afore-mentioned parts, however; rather this choice presents a few examples.

The known concept of disinfecting said accessories is based on a method uncoupled from the disinfection process of the dialysis system. For this purpose it is necessary to manually hand over all accessories to be disinfected to a disinfection apparatus separate from the dialysis system. Said separate disinfection of the accessories which is carried out independently of the disinfection of the dialysis system entails an additional process step and thus increased degree of complexity and costs.

DESCRIPTION OF THE RELATED ART

The disinfection of the accessories in a separate disinfection apparatus mentioned in the foregoing passage may be realized in various ways. A wide-spread proceeding consists in manually disinfecting the accessories using disinfection gloves and agents. Another method excels by the use of a disinfection case. The latter possesses the feature that it easily accommodates accessories. Moreover, it is designed so that it can be filled with and emptied from disinfectant without great effort. The objects to be disinfected are enclosed in such disinfection case, before the separate disinfection apparatus ensures that disinfectant is supplied to the disinfection case. At a predetermined temperature and in a predetermined quantity the disinfectant causes the accessories provided in the disinfection case to reach the desired degree of disinfection.

Generic disinfection cases are disclosed in the German utility models DE 295 03 691 U1, GM 78 14 376 U1 and GM 78 12 762 U1.

Moreover the German published patent application DE 10 2007 044 647 A1 describes a device for controlling a fluid course. It has to be classified in the field of disinfection of dialysis systems as it discloses a disinfection element which is adapted to be connected to a catheter connector and by which an exchange of solution of dialysis agents takes place. Hence it contributes to the hygiene of the dialysis unit without avoiding the afore-mentioned additional process step of separate disinfection of the accessories, however.

This is applicable mutatis mutandis to the two devices disclosed in the published patent applications DE 196 40 840 A1 and CN 102293494 (A).

SUMMARY OF THE INVENTION

In view of this state of the art, the object underlying the present invention is to provide a device which drops the additional process step of separate disinfection/purification of the accessories without accepting losses in terms of the quality of the disinfection of the accessories.

The afore-mentioned object is achieved by a blood treatment system comprising the features of the independent claim. Advantageous configurations are the subject matter of the subclaims.

The blood treatment system (such as a dialysis system) includes several components. According to aspects of the invention, these include at least one blood treatment machine (such as a dialysis machine), plural connections through which a fluid such as disinfectant may be exchanged and an internal or external disinfection case/sterilization case for accommodating medical equipment.

The blood treatment system in addition includes an internal fluid line system which is arranged, for example, inside the blood purification machine and includes several lines through which a disinfectant may flow at least during a disinfection process.

Moreover, the system according to aspects of the invention includes the afore-mentioned disinfection case which is adapted to be connected or is at least temporarily connected to the internal fluid line system at least during the disinfection process via at least one disinfection case connection so that it is adapted to be also disinfected or is also disinfected during the disinfection process. The disinfection case is suited and, respectively, provided for accommodating those additional accessories which are intended to be disinfected.

This ensures that the hygiene standards to which the accessories are subjected continue to be met as the basic procedure of disinfection with a disinfection case is known already and has turned out to be successful as mentioned in the beginning. One can even assume an increase in the hygiene factor, because on the one hand the accessories do not have to be transported—partly over rather long distances—and on the other hand the same disinfectants optimally adapted to the respective conditions are used as for the residual dialysis system. Furthermore, also the disinfection of the accessories is subjected to a central control unit described in detail in the further course of the application, which entails dependence of the two previously independent/separate disinfections also regarding their control.

In addition, a constructional design according to aspects of the invention of the disinfection case which will equally be precisely described hereinafter enables the disinfection case to be attached to the blood purification machine and, respectively, to couple the two components of "disinfection case" and "dialysis machine" in a preferably rigid manner. This feature contributes to dropping the additional process step of separate disinfection of the accessories, as they are disinfected now within the scope of the centrally controlled disinfection process of the dialysis machine.

As a consequence of said modifications according to aspects of the invention, inter alia a saving of time is resulting as compared to the conventional solutions. Apart from the increased time efficiency, the feature of the independent claim entails reduction of power consumption, thus causing the thermal efficiency of the system to increase. This is due to the fact that instead of two disinfection systems now only one disinfection system has to be operated. As a consequence, the overhead of the dialysis center are reduced. In addition, it is recalled that also the hygiene factor is increased.

Accordingly, the process of the entire dialysis center can be referred to as being improved, which emphasizes the value of the present invention.

Another advantageous embodiment consists in the fact that the blood treatment system/dialysis system includes a central electronic control unit which is electrically communicated with the blood purification machine and thus provided with information on the current operating phase thereof and which controls the blood purification machine including the already fluid-connected disinfection case so that the disinfection process is optimally adapted to the components subject to disinfection including the disinfection case and the space volume thereof. In this way a high-capacity central processing unit (CPU) may be used to optimally control the respective parameters during a disinfection process of the individual components.

Said parameters include, inter alia, the temperature of the disinfectant supplied to the fluid with heat exchangers, the respective flow rate of the hydraulic fluid through controllable flow valves, the impact/dwell times during which the disinfectant is not circulating as well as the overall duration of the disinfection process. The impact times will be mentioned once again in the further course of the application text in connection with retention times. The use of a central control unit further permits to react to unexpected events during disinfection. For example, all parameters a small selection of which has been mentioned in the foregoing paragraph may be varied where needed. This entails an enormous degree of flexibility, thus further increasing the value of the invention.

If a case supply line and a case drain line of the disinfection case are connectable to a flushing bridge selectively bridging a dialyzer of the blood treatment machine which is an integral component of the blood purification machine and which is communicated with the internal fluid line system, this involves positive aspects, for in this way a safe connection of the disinfection case to the disinfectant supply is ensured. The flushing bridge in general is part of the dialysis machine. Thus it requires no additional constructional effort. Further, for example by Hansen couplings standard components are provided already to realize a safe, low fluid loss and at the same time economic connection of the case supply line and the case drain line according to aspects of the invention to the flushing bridge.

The option of supplying the disinfection case via the flushing bridge moreover presents a solution which permits to refit existing blood treatment systems/dialysis systems so that they correspond to the apparatus according to aspects of the invention. This embodiment further offers the advantage that the disinfection case optionally may be designed to be removable from its disinfectant supply.

Another advantageous, possibly alternative embodiment excels by the fact that the case supply line and the case drain line of the disinfectant case may form a circuit having a separate disinfectant supply being communicated with the internal fluid line system. This disinfectant supply guarantees an independent supply of the disinfection case. Hence such disinfectant supply may be optimally adapted to the requirements of the disinfection case. It has to be observed that the control of the disinfectant circuit of the disinfection case continues to be carried out by the central control unit. The advantages as regards flexibility and efficiency mentioned in this context are also provided with this embodiment as a matter of course.

It is equally advantageous when the disinfection case includes connecting elements for being adapted to be rigidly coupled to the blood purification machine. It is especially emphasized that the connecting elements are configured so that they allow for an as simple mounting of the disinfection case to the blood purification machine as possible. For this, mainly positive and/or frictional connections are provided. Apart from these, the use of adhesive bonds is further imaginable. The use of connecting elements that are compatible with existing blood purification machines also in this case permits refitting existing systems to the apparatus according to aspects of the invention. In terms of construction, it is provided to attach the disinfection case laterally to an existing dialysis machine. Hence a crucial advantage of the invention consists in the fact that existing systems can be continued being used which prevents high loss in value of existing systems that have not yet been completely written off. Further, the share of investment for refitting to the apparatus according to aspects of the invention is manageable for the afore-mentioned reasons.

Another advantageous embodiment is characterized in that the disinfection case is formed integrally with the blood purification machine. Therefrom it is resulting that in terms of space the disinfection case is perfectly adapted to the requirements made to it, while the blood purification machine can be optimized regarding its constructed space required and its functional arrangement. The integration of the disinfection case into the blood purification machine moreover causes the connections for the case supply line and the case drain line to be configured as to their position adapted optimally to the other connections of the blood purification machine. In this way, the integration of the disinfection case in the blood purification machine entails mainly structural benefits that facilitate handling such as control and connection of the blood purification system.

When the disinfection case includes a lid sensor that is prepared to detect whether a case lid is in fluid-tight contact with a case body and thus the case lid is in a closed state or whether the case lid is not in fluid-tight contact with the case body and thus the case lid is in an open state, this involves further positive aspects, for that lid sensor moreover transmits the information detected by the same to the central processing unit. The latter ensures that the disinfection case is supplied with disinfectant only when the lid is in the closed fluid-tight state. The lid sensor thus contributes to the operating safety and ensures that human-caused errors, for example, such as incomplete closing of the disinfection case, are corrected before they have a negative effect. Thus the apparatus according to aspects of the invention is protected against undesired effects which may occur during the disinfection process, thus causing, apart from the operating safety, the convenience of handling the system to be increased.

According to another aspect of the present invention which possibly has to be independently claimed, the disinfection case includes a filling level sensor provided to detect the volume occupied by the disinfectant in the case body. This filling level sensor, too, is communicated with the central control unit, thereby the latter also being provided with the information about the filling level of the disinfectant in the disinfection case. Consequently, a further feature is realized by the filling level sensor, which increases the operating safety and the transparency of the individual processes. It is achieved with the information about the filling level of the disinfection case that among other factors depending on the number, the weight and the size of the individual accessories provided inside the disinfection case there is always provided the optimum quantity of disinfectant which is necessary to meet the hygiene requirements, on the one hand, and not to waste disinfectant, on the other hand. The already mentioned advantage of the increased operating efficiency of the apparatus according to aspects of the invention is thus even further increased by the filling level sensor.

It is moreover advantageous when a case volume defined by the case body and the case lid is configured as regards its geometric arrangement such that it has no undercuts and/or dead storage. Thus after each disinfection process thorough and complete flushing of the entire disinfection case is enabled, as the case volume does not include any locations where fluid residues may adsorb. This constructional design consequently contributes to the fact that the high hygiene requirements are observed and/or exceeded. A space separating element can ensure that with such clear-cut geometry of the internal volume the accessories can still be arranged in a space-saving manner. The space separating element is adapted to be inserted in the case body with positive locking and alternatively also with friction locking and can be designed such that all accessories can be disposed in a reasonable arrangement inside the case. The space separating element is formed by plural partitions and is variable as to its shape. Depending on the accessories to be disinfected, it exhibits a symmetric or asymmetric profile.

Moreover an advantageous embodiment excels by the fact that the central processing unit has such setting that variable retention times can be set during a filling operation and an emptying operation of the case volume with/from the disinfectant. It follows from the fact that these periods are controlled by the central processing unit and thus are variable that complete disinfection is always achieved irrespective of the degree of contamination of any particular accessory. The device according to aspects of the invention thus guarantees that maximum quality standards are complied with independently of the case of operation.

The disinfection process of a dialysis machine can be subdivided into the following operating phases by way of example:
   flushing the dialysis fluid
   preheating
   sucking disinfectant
   heating disinfectant
   circulating hot disinfection solution
   flushing disinfection solution and cooling down the machine.

All phases are predetermined by the central processing unit and can be realized with the arrangement of pumps and valves. It is indicated once again in this context that each of the phases is variable regarding its parameters such as time, temperature and flow rate. Furthermore, the afore-mentioned operating phases merely serve as an orientation and are not fixedly specified. For example, further operating phases may be included in the disinfection process and/or individual phases may be cancelled.

Another advantageous embodiment consists in the fact that the disinfection case includes a pressure control configured such that it detects the filling level of the disinfection case. Thus said pressure control which is equally influenced by the central processing unit constitutes an alternative concept to the already disclosed filling level sensor. Hence it can be decided in each individual case whether a sensor is used and which sensor is used. So the apparatus according to aspects of the invention does not only excel during operation by the increased flexibility but also by the choice of the individual components.

BRIEF DESCRIPTION OF THE DRAWINGS

The invention is best understood from the following detailed description when read in connection with the accompanying drawings. Included in the drawings are the following figures.

DETAILED DESCRIPTION OF THE PREFERRED EMBODIMENTS

Figure 1:
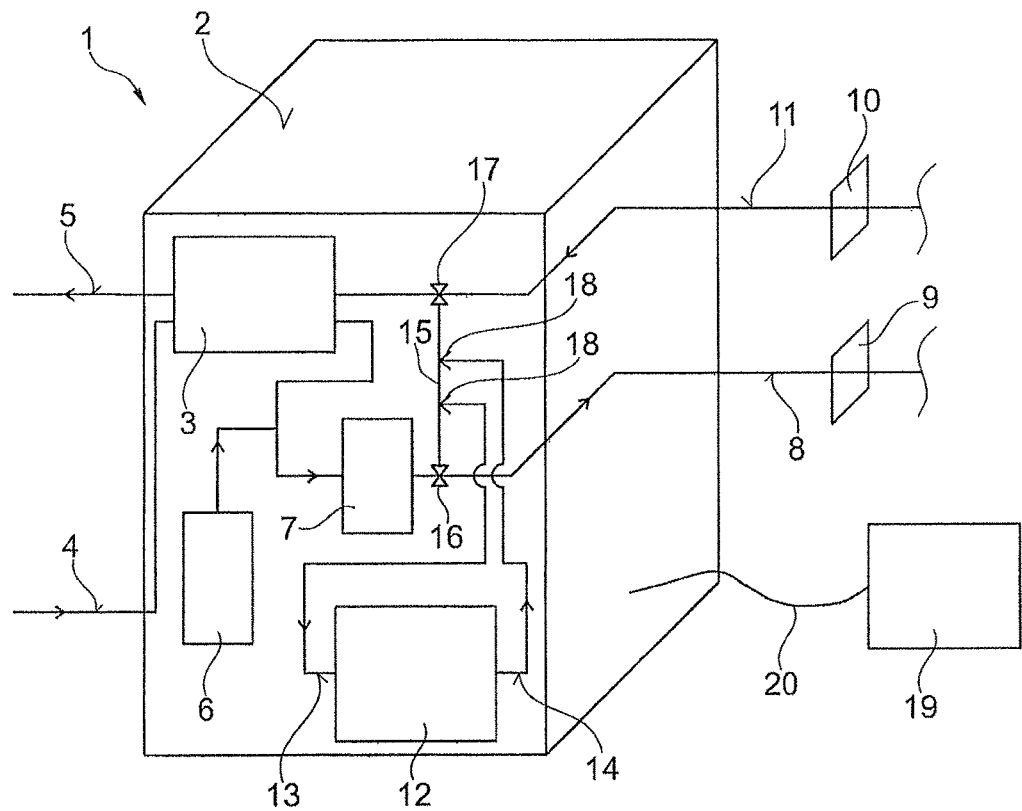
FIG. 1 shows a schematic representation of an extracorporeal blood purification system according to aspects of the invention.

An extracorporeal blood purification system 1 according to aspects of the invention includes plural components. These include at least an extracorporeal blood purification machine 2 providing dialysis solution, for example. The structure of an extracorporeal blood purification machine is known to those skilled in the art from the German published patent application DE 103 19 220A1. Furthermore EP 1 491 222 A1 discloses such machine so that it is not necessary in this context to discuss the structure of an extracorporeal blood purification machine in detail.

The extracorporeal blood purification machine 2 according to aspects of the invention communicates with a central processing unit 19 with an electric connection 20. The central processing unit 19 has access to all fluid adjusting components of the system. Said fluid adjusting components denote valves such as stop valves/excess pressure valves/check valves/pressure and directional valves as well as pumps of any type that transport fluid in a fluid system. The positions/flow rates/operating phases of the individual fluid adjusting components are specified by the central processing unit 19. The central processing unit 19 further controls the individual phases of the blood treatment/blood purification/dialysis processes. After each blood treatment process the system undergoes a disinfection process. According to aspects of the invention, the latter is equally controllable by the central processing unit 19 and includes, apart from the blood treatment machine 2, also a disinfection case 12 and accessories contained therein.

FIG. 1 represents a schematic structure of the extracorporeal blood purification system 1 according to aspects of the present invention. Inside the blood purification machine 2 the system includes a heat exchanger 3 which is suited for transmitting recuperation heat from an outflowing fluid to an inflowing fluid. The inflowing fluid enters into the extracorporeal blood purification machine via a supply line 4. Accordingly, the outflowing fluid leaves the machine via a drain line 5.

Another central component of the blood purification machine 2 is a fluid conditioning component 6 which is communicated with the supply line 4 such that it conditions the inflowing fluid, for example (osmosis) water, to form a dialysis fluid. The dialysis fluid is suited for carrying out blood purification on a patient. Also balancing means 7, as known from the afore-cited European application document EP 1 491 222 A1, is of salient importance to a reliable operation of the blood purification machine 2. The dialysis fluid leaves the balancing means 7 via a fresh dialysis fluid line 8. The latter leads the dialysis fluid to a first connecting valve means, preferably a dialysis membrane coupling 9. With said first dialysis membrane coupling 9 the fresh dialysis fluid line 8 is adapted to be coupled to the inlet of a membrane unit (dialyzer) at which a blood treatment/blood purification/dialysis process takes is carried out. Said membrane unit (dialyzer) usually is a single-use product; therefore the detailed representation thereof is renounced in FIG. 1.

A second connecting valve means, preferably a dialysis membrane coupling 10, connects a used dialysis fluid line 11 to an outlet of the membrane unit (dialyzer). In this way the used dialysis fluid line 11 enables the used dialysis fluid to be returned. After passing the heat exchanger 3 the used dialysis fluid leaves the blood purification machine 2 via the drain line 5.

In order to maintain the complicated design of the system clear, only few components of the extracorporeal blood treatment machine 2 are shown in FIG. 1.

FIG. 1 does not constitute any limiting embodiment either in terms of the number or in terms of the arrangement and order of the components. As regards further possible parts of the extracorporeal blood treatment machine 2, the afore-cited state of the art is referred to.

In accordance with the invention, the extracorporeal blood purification system 1 includes, in addition to the generally known blood treatment machine 2, a preferably external disinfection case 12 for receiving medical equipment as possibly required especially for the blood treatment with the blood treatment system according to aspects of the invention. Fluid may be supplied to the said case with a case supply line 13 and fluid can be drained with a case drain line 14. According to aspects of the invention, the disinfection case 12 may be designed either as an external component adapted to be preferably rigidly coupled to the blood treatment/purification machine 2 or it can be formed integrally with the blood purification machine 2. In FIG. 1 a blood treatment system comprising an integrated disinfection case 12 is shown, wherein in this case a loading door or a loading cover is provided at the housing of the blood purification machine 2 via which the disinfection case 12 is directly loaded/unloaded or the latter may be removed from the blood purification machine 12 for loading/unloading.

It is further possible/preferred according to aspects of the invention to couple or provide the disinfection case 12 with a generally known flushing bridge 15 of the blood purification machine 2 and/or with a separate independent disinfection circuit. FIG. 1 illustrates the embodiment with the flushing bridge 15. A detailed structure of a flushing bridge is known to those skilled in the art from DE 10 2013 107 323 A1; therefore it is not further discussed in detail within the scope of this application document.

The flushing bridge 15 is a sort of short-circuit between the fresh dialysis fluid line 8 and the used dialysis fluid line 11. During the dialysis process the flushing bridge 15 is separated from the dialysis fluid circuit with stop valves 16, 17. The stop valves 16, 17 are opened only in the case of a disinfection process so that a disinfectant can flow/flows through the flushing bridge 15. In addition, a valve may be formed at each of the fresh dialysis fluid line 8 and the used dialysis fluid line 11 so as to better uncouple the membrane unit (dialyzer) from the fluid circuit during the disinfection operation. The case supply line 13 and the case drain line 14 are adapted to be coupled or are coupled to the flushing bridge 15 by way of flushing bridge ports 18. When a disinfection case is connected to the flushing bridge 15 for a disinfection operation, additionally the fluid flow through the flushing bridge 15 is blocked by a valve so that the fluid is guided through the disinfection case (now constituting the possibly external flushing bridge).

Alternatively to the stop valves 17 and 16 also a switch point for switching over the fluid flow may be provided at each branch to the flushing bridge 15 from the fluid line. For this purpose, also a multiple-way cock could alternatively be provided at the branch of the flushing bridge 15 from the fluid line.

The switching of the fluid flow via a valve, a multiple-way cock or any other switch point, for example, may be carried out manually or automatically. For instance, a user could manually change over the multiple-way cock. As an alternative, the change-over could be performed automatically, however, for example after a user having input an appropriate instruction into the control unit. Also, the central processing unit could detect from the operating data of the blood treatment system 1 that a disinfection process is required and could change over switch points or valves or multiple-way cocks fully automatically and without any further user input and initiate the disinfection process.

When using a disinfection case that is not permanently integrated in the blood treatment system, it is furthermore possible that the physical coupling of the disinfection case to the ports of the blood treatment/purification machine 2 per se causes the purification fluid to bypass into the external disinfection case 12 according to the principle of a plug-and-play connection.

As soon as the disinfection case 12 is connected to a disinfection cycle via the internal flushing bridge 15, the disinfectant flows through the disinfection case 12 while being driven by pumps not shown here. Accordingly, disinfection/purification of the accessories arranged inside the disinfection case 12 takes place. The adjustable parameters such as the flow rate and the flow time as well as the temperature of the disinfectant are adapted by the central processing unit 19 so that the accessories are adapted to be fully disinfected/are fully disinfected. A sensor system not further specified within this published application document can be used to check in the course of the disinfection process in how far the degree of contamination of the accessories decreases over time.

The central processing unit 19 is equally part of the extracorporeal blood purification system 1 and communicates with the blood purification machine 2 preferably via the electric connection 20. In this way the central processing unit 19 is adapted to be adjusted/programmed/arranged so that the extracorporeal blood purification system is variable as regards the fluid transport and can react in a flexible manner, for, apart from the stop valves 16, 17 shown in FIG. 1, the system includes further valve units, as afore-mentioned, which are controllable/controlled by the central processing unit. For reasons of clarity, those further valve units that are known to those skilled in the art from the afore-cited state of the art are not illustrated here.

Figure 2:
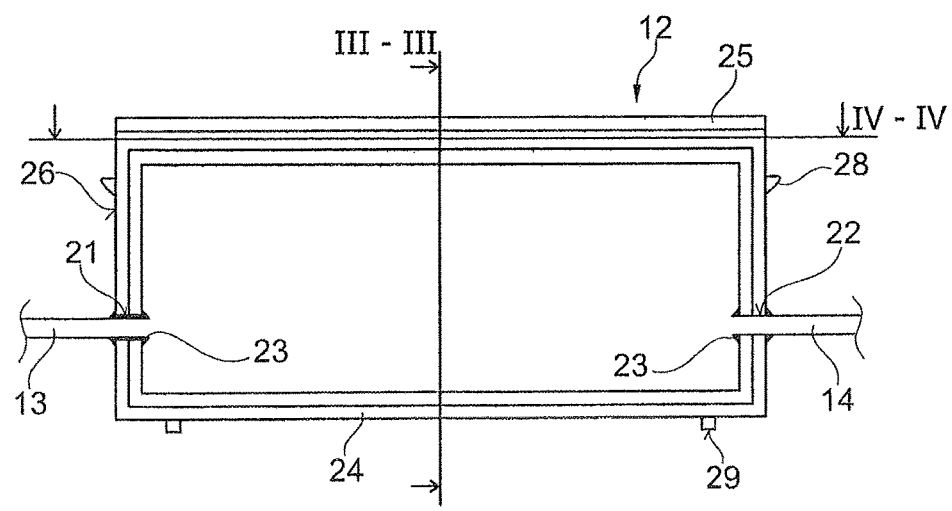
FIG. 2 shows a sectional view across a disinfection case according to aspects of the invention in a closed state.
Figure 3:
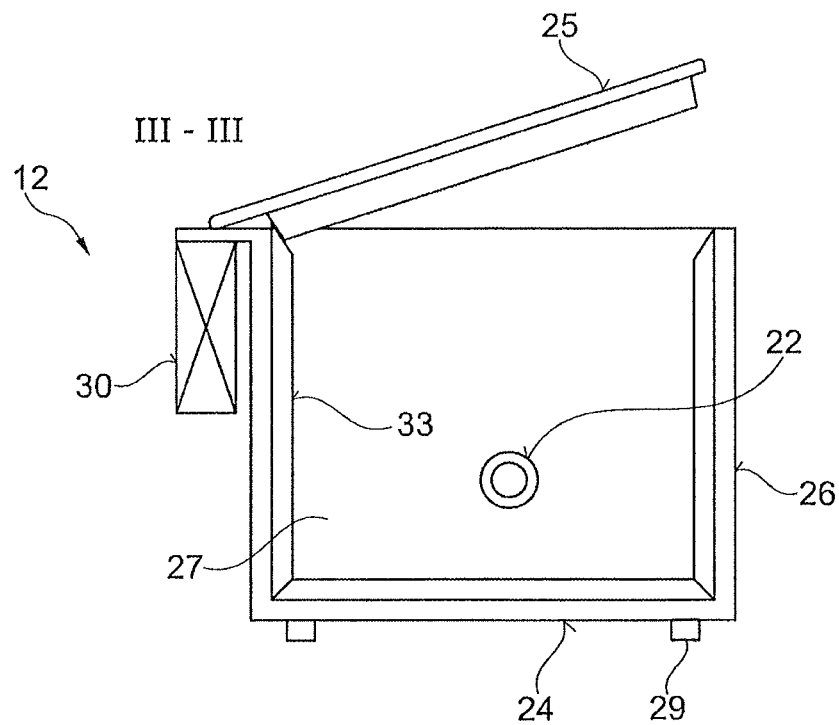
FIG. 3 shows a sectional view along a further sectional plane across a disinfection case according to aspects of the invention from FIG. 2 in an open state.
Figure 4:
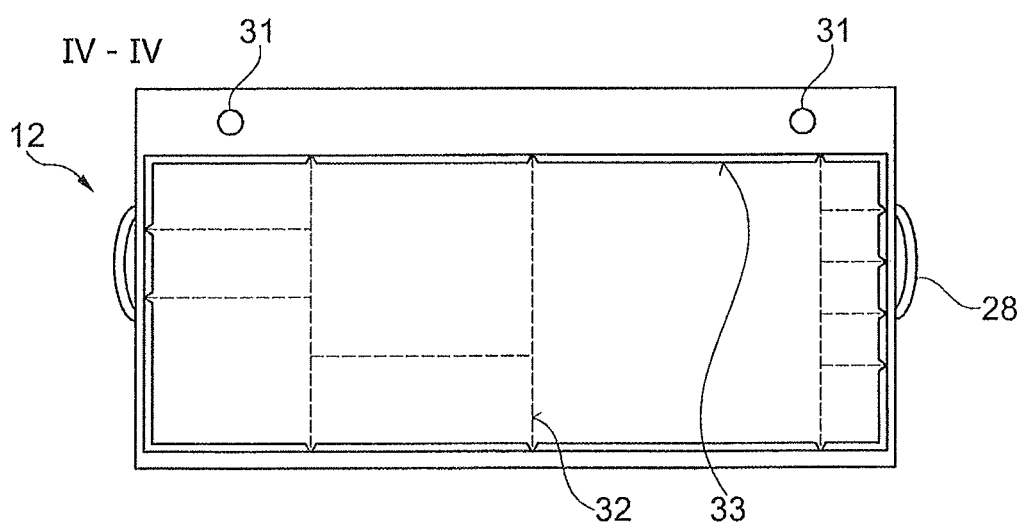
FIG. 4 shows a sectional view along a further sectional plane across a disinfection case according to aspects of the invention from FIGS. 2, 3.

All of the accompanying FIGS. 2, 3 and 4 represent a disinfection case 12 adapted to be coupled to the blood purification machine 2 as an external component.

Concerning an embodiment in which the disinfection case 12 has an approximately rectangular base area and contacts the blood purification machine 2 at one of two longer sides, FIG. 2 represents a section along the front plane. This section is taken such that both the case supply line 13 and the case drain line 14 are located in the sectional plane. The case supply line 13 is connected to the disinfection case 12 via a supply port 21. This is analogously applicable to the case drain line 14 which is connected to the disinfection case 12 via a drain port 22. These connections between the lines and the ports may be established by various coupling elements such as integrated couplings or Hansen couplings. Sealing elements 23 constitute part of the supply port 21 and, respectively, drain port 22. The sealing elements 23 provide for fluid-tight connection between the case supply line 13 and the case drain line 14, respectively, and the disinfection case 12.

The embodiment illustrated in FIG. 2 includes an arrangement in which the supply port 21 and the drain port 22 are arranged at the same height on opposite sides. It is mentioned in this context that the apparatus according to aspects of the invention is by no means limited to this embodiment. It is certainly imaginable that the supply port 21 is arranged to be higher than the drain port 22 or vice versa. Further, the apparatus is flexible as regards the arrangement of the ports. In a different embodiment, the supply port 21 and the drain port 22 are disposed at the same or at adjacent side walls, for example. This may be desirable as regards the flow characteristics of the disinfectant and the turbulences resulting therefrom inside the disinfection case 12 so as to promote a more efficient disinfection process. Also, an arrangement of the ports in a case bottom 24 or a case lid 25 may be intended. Depending on the arrangement of the accessories inside the disinfection case 12, this may have a positive effect on the retention periods.

Case walls 26 together with the case bottom 24 form a case body 27 which can be closed in a fluid-tight manner by the case lid 25. In the embodiment shown in FIGS. 2 to 4 the case lid 25 is a folding lid supported on one side. Moreover, also two-part folding lids supported on both sides and/or shift devices and/or separate lid devices are possible as a closing mechanism. As regards its geometric shape, the case lid 25 can be variably designed and is not restricted to the mostly planar shape of the Figures. For example a bell/bulge-shaped and/or convex design may be desirable so as to enlarge the volume of the case body 27 and thus to be able to receive more accessories.

For the purpose of facilitating the handling of the disinfection case 12 it is possible to dispose handles 28 at the case walls 26. Just as the feet 29, they have no direct function during operation. Rather, they are adapted to facilitate the process of replacing the case, as they enable an operator to easily place and transport/lift the disinfection case 12. Concerning the handles 28 it is suggested to manufacture them of different material(s) than the residual case. In this way the handles 28 are prevented from being heated by a disinfectant which may reach temperatures of 70° C. to 90° C. during the disinfection process and thus always can be gripped. For the material(s) of the disinfection case 12 primarily plastic materials are suggested.

The section across the front plane in FIG. 2 equally indicates the two sectional planes from FIG. 3 and FIG. 4. The Roman figures III and, respectively, IV are used for emphasizing the latter sectional planes.

Accordingly, FIG. 3 represents a section in the sagittal plane of the disinfection case 12 from FIG. 2. The case body 27 includes connecting elements 30 on the side facing the dialysis machine 2. They are a central component of the disinfection case 12 as they enable the afore-mentioned external configuration of the disinfection case 12 to be rigidly connectable to the dialysis machine 2. The connecting elements 30 are causing a positive and/or frictional and/or adhesive connection of the two components of "disinfection case 12" and "dialysis machine 2". As regards their arrangements, they are by no means limited to the shape indicated in FIG. 3. They may be formed on each of the case walls 26, optionally also on plural case walls 26 and/or on the case lid 25 and/or on the case bottom 24. Preferably, the connecting elements 30 are configured so that they allow lateral mounting to the dialysis machine 2.

In the embodiment shown in FIG. 2 it is clearly evident that the case body 27 includes no dead storages and/or undercuts, thus enabling thorough bacteria-free flushing of the disinfection case 12.

FIG. 4 illustrates a section across the transversal plane of the case body 27. The case lid 25 is not shown in FIG. 4. A lid fastening 31 is realized, by way of example, by two openings in FIG. 4. Said openings may fix the case lid 25 while a bearing not shown is in charge of the rotatability of the case lid 25. The lid fastening 31 is merely schematic and specifies no limiting embodiment. Schematically indicated partitions 32 have the function of offering a fixation to the accessories. They may be freely disposed and are in positive, alternatively also frictional and/or adhesive connection, for example, with an inner case wall 33.

The invention claimed is:

1. An extracorporeal blood purification system comprising:
   an extracorporeal blood purification machine configured for a centrally controlled disinfection process following a blood purification process;
   an internal fluid line system within the extracorporeal blood purification machine through which a disinfectant may flow at least during the disinfection process, wherein the internal fluid line system has a fresh dialysis fluid line and a used dialysis fluid line, the fresh dialysis fluid line and the used dialysis fluid line configured to connect to a dialyzer of the extracorporeal blood purification machine;
   a flushing bridge integral to the internal fluid line system placed within the extracorporeal blood purification machine, the flushing bridge arranged as a single separate line connected between the fresh dialysis fluid line and the used dialysis fluid line, the flushing bridge configured to short-circuit the dialyzer of the extracorporeal blood purification machine a plurality of flushing bridge ports arranged on the flushing bridge between the fresh dialysis fluid line and the used dialysis fluid line; and a disinfection case having a case supply line connected to one of the plurality of flushing bridge ports and a case drain line connected to another of the plurality of flushing bridge ports, the disinfection case configured to receive accessories, wherein, at least during the disinfection process, the one of the plurality of flushing bridge ports supplies fluid to the disinfection case via the case supply line, and the another of the plurality of flushing bridge ports drains the fluid from the disinfection case via the case drain line.

2. The extracorporeal blood treatment system according to claim 1, wherein the disinfection case is external to the extracorporeal blood purification machine.

3. The extracorporeal blood purification system according to claim 1, wherein fluid guiding means are provided on at least one of the blood treatment machine or the disinfection case for circulating fluid flow in a fluid guiding system either in a closed internal manner within the blood purification machine and for guiding the fluid flow through the disinfection case during the disinfection process.

4. The extracorporeal blood treatment system according to claim 3, wherein the fluid guiding means constitute a respective switch point, a valve or a multiple-way cock.

5. The extracorporeal blood treatment system according to claim 3, wherein the fluid guiding means are adapted to be controlled manually or automatically for changing over the fluid flow between a closed internal fluid circulation within the blood purification machine and the fluid flow through the disinfection case during the disinfection process.

6. The extracorporeal blood purification system according claim 2, wherein the case supply line and the case drain line of the disinfection case form a circuit having a separate disinfectant supply being communicated with the internal fluid line system.

7. The extracorporeal blood purification system according to claim 1, wherein the disinfection case includes mechanical connecting elements so that an exterior of the disinfection case can be rigidly coupled to the blood purification machine.

8. The extracorporeal blood purification system according to claim 1, wherein the disinfection case is formed integrally with the blood purification machine.

9. The extracorporeal blood purification system according to claim 1, wherein the disinfection case includes a lid sensor provided for detecting whether a case lid is in fluid-tight contact with a case body and hence the case lid is in a closed state or the case lid is not in fluid-tight contact with the case body and hence the case lid is in an open state.

10. The extracorporeal blood purification system according to claim 1, wherein the disinfection case includes a filling level sensor provided for detecting the volume occupied by the disinfectant inside the case.

* * * * *